(12) United States Patent
Kumar

(10) Patent No.: US 6,315,562 B1
(45) Date of Patent: *Nov. 13, 2001

(54) IMPLANT CARRIER WITH GRIPPING FINGERS

(75) Inventor: Ajay Kumar, Loma Linda, CA (US)

(73) Assignee: Nobel Biocare USA, Inc., Yorba Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/455,034

(22) Filed: Dec. 6, 1999

Related U.S. Application Data

(63) Continuation of application No. 09/227,069, filed on Jan. 5, 1999, now Pat. No. 6,159,008.
(60) Provisional application No. 60/092,674, filed on Jul. 13, 1998.

(51) Int. Cl.⁷ ....................................................... A61C 8/00
(52) U.S. Cl. ............................................ 433/173; 433/141
(58) Field of Search ................................... 433/173, 141; 623/17.16; 206/63.5

(56) References Cited

U.S. PATENT DOCUMENTS

| | | | |
|---|---|---|---|
| 2,347,567 | 4/1944 | Kresse | 424/487 |
| 3,346,135 | 10/1967 | Haitsch | 206/265 |

(List continued on next page.)

FOREIGN PATENT DOCUMENTS

| | | |
|---|---|---|
| G 90 14 729.4 | 1/1991 | (DE) . |
| WO 96/25895 | 8/1996 | (WO) . |
| WO 98/52490 | 11/1998 | (WO) . |
| WO 98/53755 | 12/1998 | (WO) . |

*Primary Examiner*—John J. Wilson
(74) *Attorney, Agent, or Firm*—Knobbe, Martens, Olson & Bear, LLP

(57) ABSTRACT

A carrier, for a dental implant kit, for reliably and releasably holding the dental implant. The carrier incorporates a plurality of flexible fingers for engaging a screw of the dental implant kit in which the screw is threadably engaged with the implant. The fingers latch on to the screw by providing a mechanical lock in a groove of the screw. The fingers can further grip the screw by applying a generally radial compressive force on the screw. Advantageously, the resiliency and structure of the carrier fingers not only provides a reliable long-term grip on the screw, and hence the implant, but also permit the screw, and hence the implant, to be conveniently attached and detached from the carrier.

54 Claims, 6 Drawing Sheets

U.S. PATENT DOCUMENTS

| | | | |
|---|---|---|---|
| 4,158,256 | 6/1979 | Wiland et al. | 433/219 |
| 4,187,609 | 2/1980 | Edelman | 433/176 |
| 4,465,463 | 8/1984 | Olde | 433/141 |
| 4,553,942 | 11/1985 | Sutter | 433/225 |
| 4,600,388 | 7/1986 | Linkow | 433/176 |
| 4,722,688 | 2/1988 | Lonca | 433/173 |
| 4,787,278 * | 11/1988 | Bononi | 81/438 |
| 4,856,648 | 8/1989 | Krueger | 206/63.5 |
| 4,856,994 | 8/1989 | Lazzara et al. | 433/173 |
| 4,955,811 | 9/1990 | Lazzara et al. | 433/173 |
| 5,030,096 | 7/1991 | Hurson et al. | 433/173 |
| 5,062,800 | 11/1991 | Niznick | 433/173 |
| 5,100,323 | 3/1992 | Friedman et al. | 433/173 |
| 5,105,690 | 4/1992 | Lazzara et al. | 81/436 |
| 5,108,288 | 4/1992 | Perry | 433/173 |
| 5,158,458 | 10/1992 | Perry | 433/174 |
| 5,213,500 | 5/1993 | Salazar et al. | 433/173 |
| 5,254,005 | 10/1993 | Zuest | 433/173 |
| 5,290,171 | 3/1994 | Daftary et al. | 433/163 |
| 5,302,125 | 4/1994 | Kownacki et al. | 433/173 |
| 5,306,309 | 4/1994 | Wagner et al. | 623/17.16 |
| 5,312,254 | 5/1994 | Rosenlicht | 433/173 |
| 5,322,443 | 6/1994 | Beaty | 433/173 |
| 5,368,160 | 11/1994 | Leuschen et al. | 433/174 |
| 5,417,570 | 5/1995 | Zuest et al. | 433/173 |
| 5,437,550 | 8/1995 | Beaty et al. | 433/173 |
| 5,453,010 | 9/1995 | Klein | 433/221 |
| 5,462,436 | 10/1995 | Beaty | 433/173 |
| 5,507,643 | 4/1996 | Klein | 433/141 |
| 5,538,428 | 7/1996 | Staubli | 433/173 |
| 5,558,230 | 9/1996 | Fischer et al. | 433/174 |
| 5,569,037 | 10/1996 | Moy et al. | 433/173 |
| 5,582,299 | 12/1996 | Lazzara et al. | 206/63.5 |
| 5,622,500 | 4/1997 | Niznick | 433/173 |
| 5,636,991 | 6/1997 | Mays | 433/220 |
| 5,683,464 | 11/1997 | Wagner et al. | 623/17.16 |
| 5,692,904 | 12/1997 | Beaty et al. | 433/173 |
| 5,755,575 | 5/1998 | Biggs | 433/173 |
| 5,904,483 | 5/1999 | Wade | 433/173 |
| 5,961,330 | 10/1999 | Hanson | 433/173 |
| 5,964,591 | 10/1999 | Beaty et al. | 433/173 |

* cited by examiner

IMPLANT CARRIER WITH GRIPPING FINGERS

Related Applications

This application is a continuation of U.S. application Ser. No. 09/227,069, filed Jan. 5, 1999, now U.S. Pat. No. 6,159,008, which claims priority to U.S. Provisional Application No. 60/092,674, filed Jul. 13, 1998.

BACKGROUND OF THE INVENTION

1. Field of the Invention

The present invention relates generally to dental implants and, in particular, to a dental implant carrier with fingers for reliably and releasably holding the dental implant assembly.

2. Background of the Related Art

In the 1930's, the first attempts to provide dental implants were unpredictable partially because of the designs and materials that were used, and partially because of poor technique. During the 1960's and 1970's, the designs, materials and techniques utilized were radically altered and predictably more acceptable results began to be achieved. Since then many further improvements have been made in this field though there is still room for additional progress, advancement and refinement.

Dental implants are surgically implanted in a patient's jaw bone to provide anchors for prosthetic devices such as crowns, bridges, dentures and the like. One modem and popular dental implant kit is packaged in a unit comprising a carrier, an insertion tool, an insertion tool screw, and an implant component or "implant". Typically, the screw traverses a central opening in the insertion tool and is threaded into a central threaded opening in the implant, thereby attaching the bottom end of the insertion tool to the top of the implant. A carrier or handle engages the screw and/or insertion tool. The carrier is used to hold the dental implant within the package and during transport to a surgical site. The dental implant package is usually sterilized and the carrier allows the dental implant to be transported with minimal risk of contamination due to contact with the operator. The carrier also permits the implant to be partially or fully inserted into a drilled hole or osteotomy in the jaw bone of a patient. The carrier can then be pulled and/or loosened and removed and, if needed, a wrench can be used to seat the implant subgingivally into the bone.

There are several potential problems associated with conventional dental implant carriers. By way of example, a carrier 100 which is widely used today, is illustrated in FIGS. 1A and 1B. FIG. 1A shows a partially sectional view of the carrier 100 engaged with a screw 102, and also shows an insertion tool 104. FIG. 1B is a sectional view of the carrier 100.

Referring to FIGS. 1A and 1B, typically, the upper end of the screw 102 has a groove 108 which is circumscribed by a small O-ring 106. The O-ring 106 creates an interference type fit with the smooth inner bore 110 of the carrier 100, thereby releasably securing the insertion tool screw 102 to the carrier 100. Of course, the screw will be threadably attached to an implant (not shown), so that the carrier 100 holds the entire dental implant assembly including the screw 102, the insertion tool 104 and the implant (not shown). Optionally, a healing screw (not shown) may also be included in the dental implant kit and typically resides in the upper part of the central bore of the carrier 100.

This gripping mechanism incorporated by the above-mentioned interference fit between the O-ring and the carrier smooth bore can pose some problems. The O-ring, particularly since it is substantially stretched or "deformed", may degrade and/or lose its resilience with time which can affect the quality of the above-mentioned interference fit and increases the risk of the carrier losing its grip on the dental implant, thereby permitting the dental implant to slide out. This is conceivable because it is not uncommon for a dental implant kit to be transported by common carriers and be exposed to variations in temperature and to vibrations on-the-shelf or in storage for a period of several years. It is especially detrimental and inconvenient if the dental implant slips out of the carrier during a dental procedure.

Therefore, it would be desirable to provide a dental implant carrier with a releasable gripping mechanism that can effectively and reliably grip a dental implant over a substantially prolonged period of time. Subsequently, such an implant carrier may reliably be used in dental procedures without posing a risk to the well-being of a patient.

SUMMARY OF THE INVENTION

The present invention overcomes some or all of the afore-mentioned disadvantages by providing a carrier, for a dental implant kit or assembly, with a plurality of flexible fingers for reliably and releasably retaining the dental implant, thereby, advantageously adding to the safety of the dental procedure.

In one preferred embodiment of the present invention, the implant carrier includes three flexible fingers. Preferably, the fingers are disposed in a substantially central cavity of the carrier. Preferably, the top ends of the respective fingers are attached to the wall of the carrier cavity such that the fingers are slightly spaced away from the cavity wall. The body portions of the respective fingers are generally curved and extend downwards while the bottom ends of the respective fingers bulge or project generally radially into the carrier cavity.

Preferably, the dental implant kit also includes a screw which resides at least partially in the carrier cavity. The screw preferably has a groove which is engaged by the bulging or projecting bottom ends of the respective fingers. The head of the screw is preferably substantially enveloped by the body portions of the respective fingers. Preferably, the screw traverses a substantially central cavity of an insertion tool of the dental implant kit and has a lower threaded portion which threadably engages the implant. The upper portion of the insertion tool is adapted to substantially irrotationally engage the lower end of the carrier cavity by having a hex configuration. The insertion tool and the implant are substantially irrotationally engaged with one another, During assembly of the dental implant kit, the screw is inserted into the carrier cavity and the carrier fingers initially flex generally radially outwards as they engage the head of the screw, and are then resiliently displaced generally radially inwards as the bulging bottom ends of the respective fingers engage the groove of the screw. Advantageously and preferably, in the assembled state of the dental implant kit, the carrier fingers provide a redundant latching mechanism to capture the screw, and hence the implant since the screw is threadably engaged with the implant, by mechanically locking into the screw groove and by applying a generally radial compressive force to grip the screw. Advantageously and preferably, the fingers are unflexed or only slightly flexed in the assembled state of the dental implant kit such that the resilient displacement of the fingers is none or small when the screw is gripped by the carrier fingers. Desirably, this eliminates or minimizes the "deformation" or "prestressing" of the fingers in the assembled state and permits a substantially long on-the-shelf and storage life for the dental implant kit. It will be apparent to those skilled in the art that the present invention may be practiced with the carrier fingers configured to apply less, more or no radial compressive force on the screw, as required or desired. During the removal of the screw from the carrier, the fingers initially flex generally radially outwards as the bulging bottom ends of the respective fingers slip out of the screw groove and engage the screw head until the screw head is released from the fingers which are then resiliently displaced generally radially inwards to an unflexed position.

The utility of the present invention will be readily apparent to those skilled in the art from the detailed description and drawings which follow. Advantageously, the resiliency and structure of the carrier fingers not only provides a reliable long-term grip on the screw, and hence the implant, but also permit the screw, and hence the implant, to be conveniently attached and detached from the carrier.

Other specific provisions and advantages of the present invention will become apparent from a reading and study of the specification, claims and figures. As will be realized by those skilled in the art the invention is capable of modifications in various respects, all without departing from the scope and utility of the invention as disclosed herein. Accordingly the specification and figures should be regarded as illustrative in nature, and not as restrictive.

DETAILED DESCRIPTION OF THE PREFERRED EMBODIMENT

Figure 2:
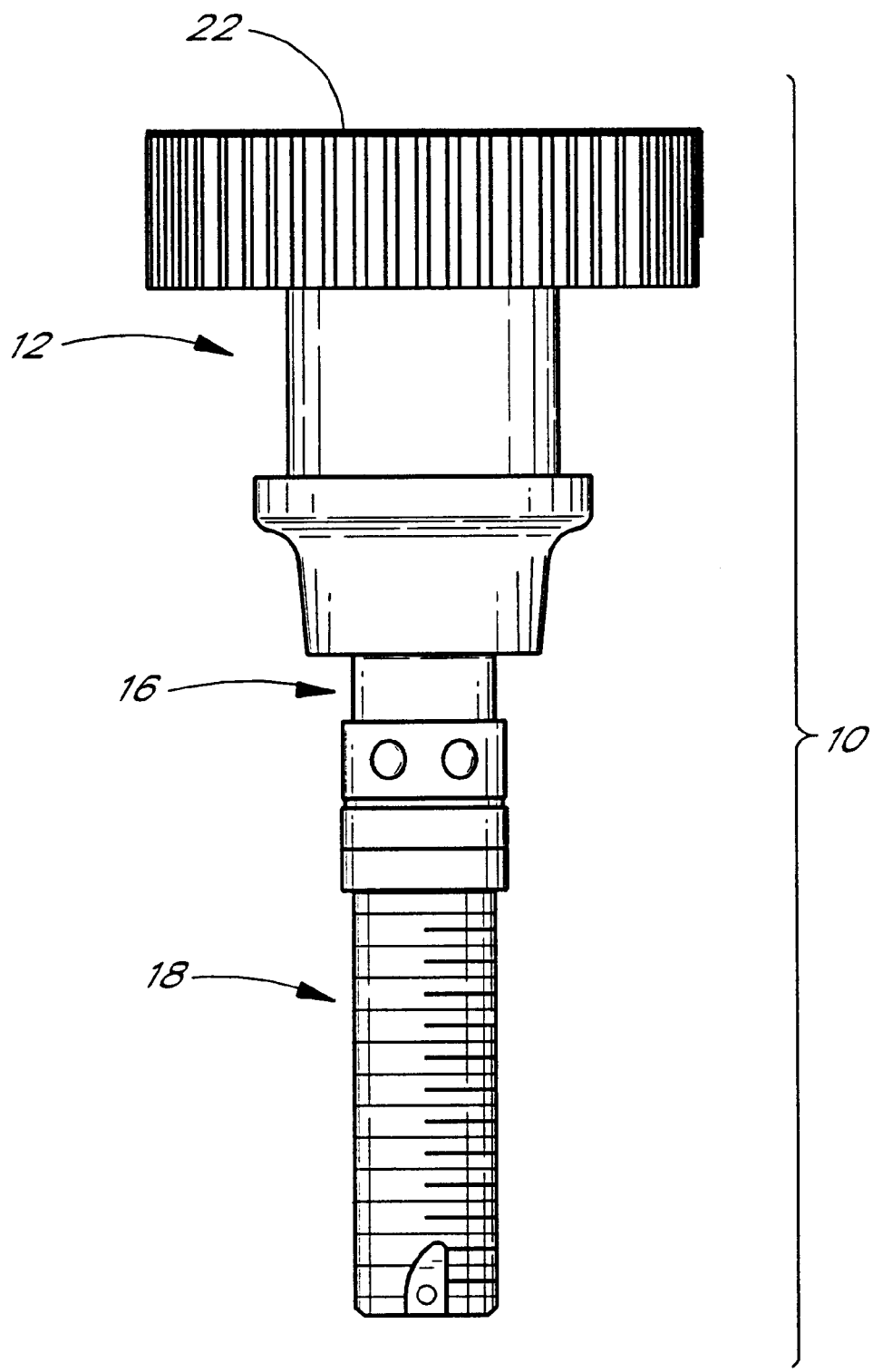
FIG. 2 is a side elevation view of a dental implant kit including an implant carrier in accordance with one preferred embodiment of the present invention.
Figure 3:
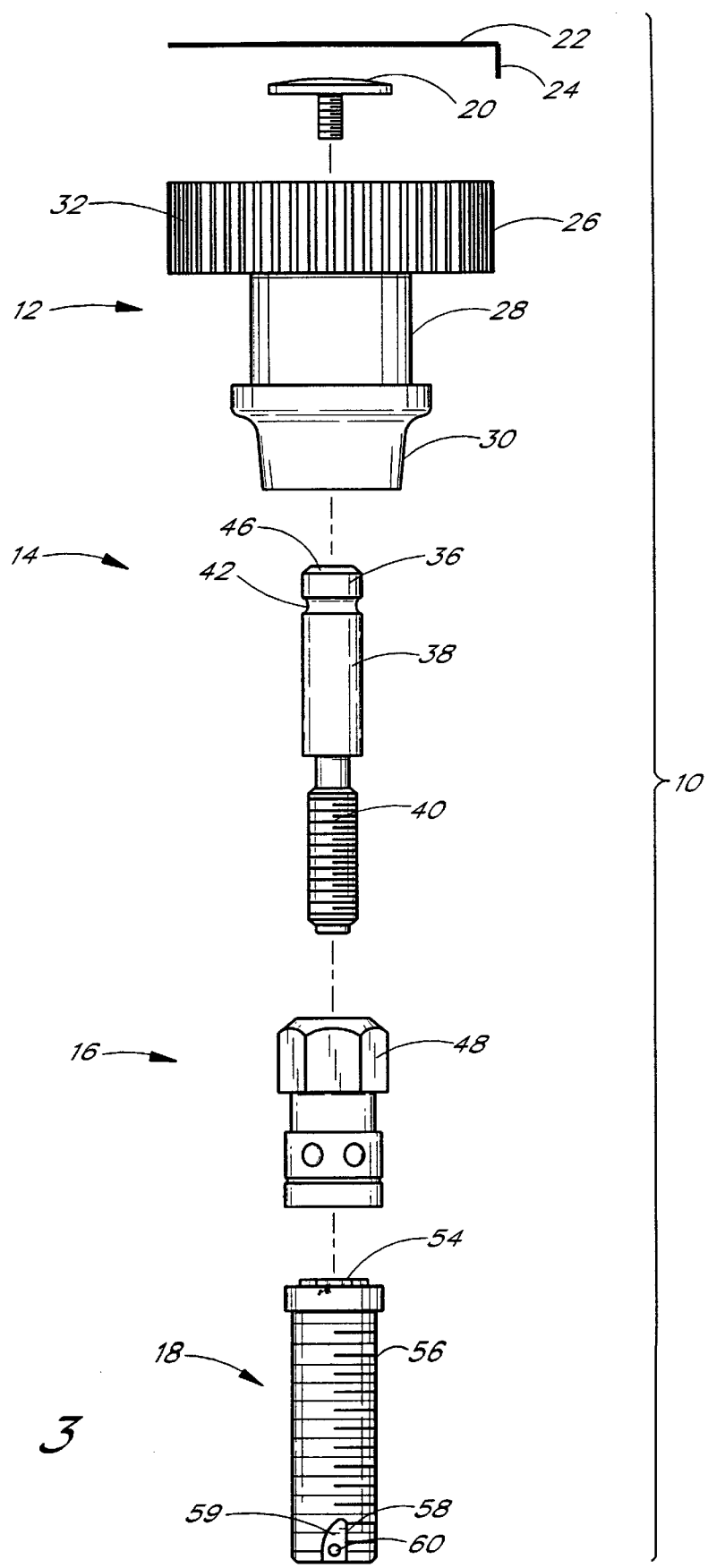
FIG. 3 is an exploded side elevation view of the dental implant kit of FIG. 2.

Referring to the drawings, and particularly to FIGS. 2 and 3, one preferred embodiment of a dental implant kit, assembly or combination 10 constructed and assembled in accordance with the invention includes a dental carrier 12, an insertion tool screw 14, an insertion tool 16 and an implant 18. Optionally, a healing screw 20 may also be included in the dental implant kit 10. The carrier 12 reliably and releasably grips the screw 14 and serves as a handle for transporting the dental implant kit to a surgical site and facilitates insertion of the implant 18 into a drilled hole or osteotomy in a jaw bone by serving as a driver. In one preferred embodiment of the present invention the dental implant kit of FIG. 2 is packaged in a sterile environment.

Figure 4A:
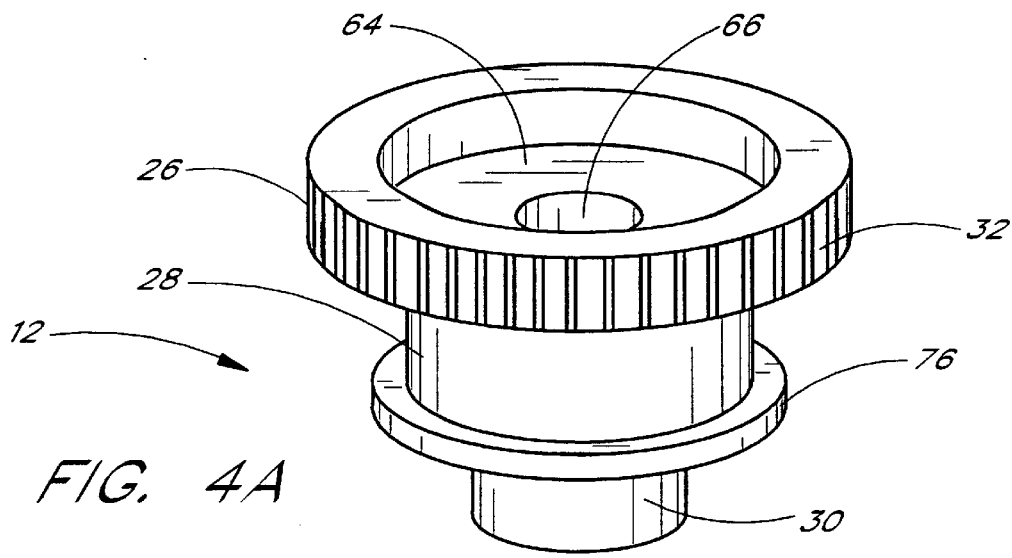
FIG. 4A is a perspective view of the implant carrier of FIG. 2.
Figure 4B:
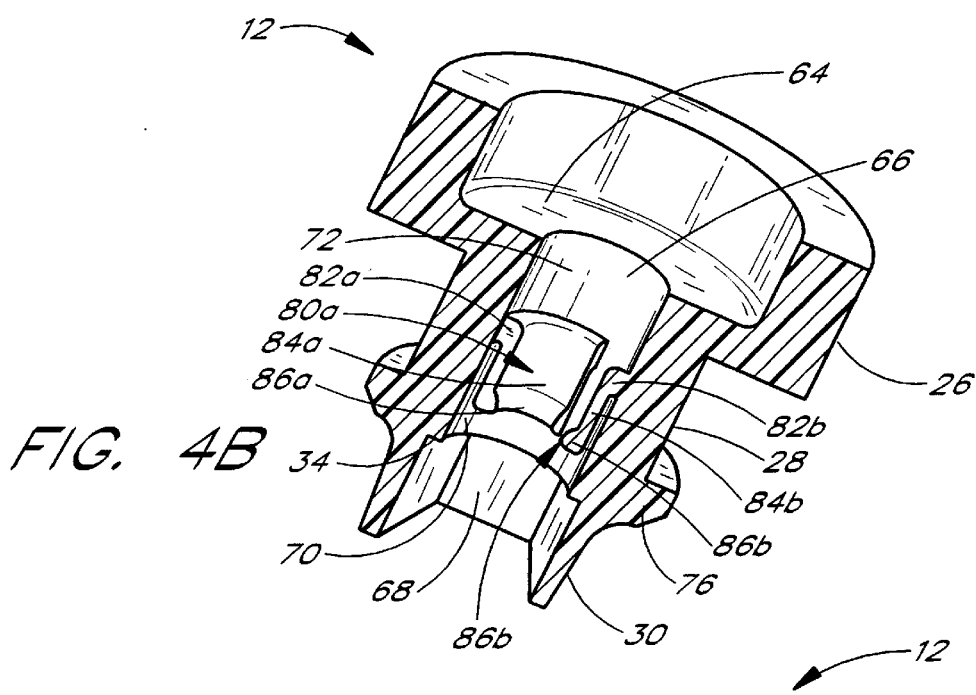
FIG. 4B is a sectional perspective view of the implant carrier of FIG. 2.
Figure 4C:
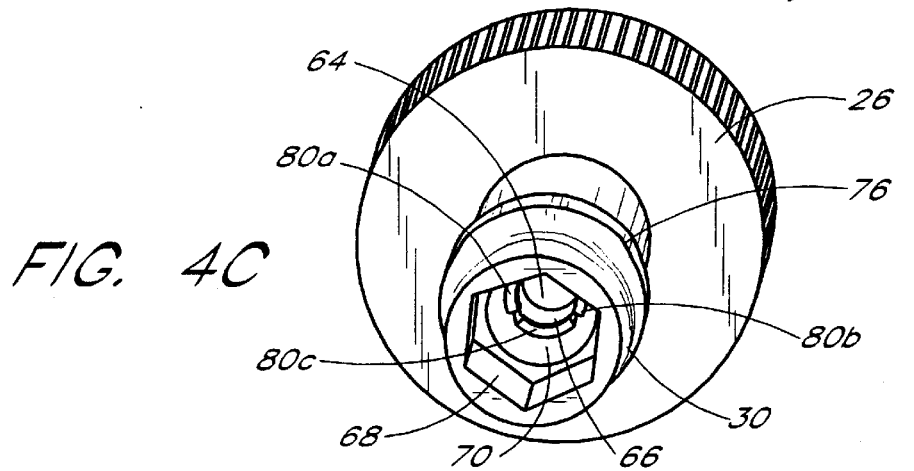
FIG. 4C is a bottom perspective view of the implant carrier of FIG. 2.

Preferably, and as best shown in FIGS. 4A, 4B and 4C, the implant carrier 12 comprises an anterior section 26, a medial section 28 and a posterior section 30. The anterior section 26 is preferably generally cylindrical in shape and has a substantially central cylindrical cavity 64. The outer curved surface 32 of the anterior section 26 is preferably ridged, grooved or knurled to provide a convenient gripping surface.

Preferably, the medial section 28 of the carrier 12 (see, for example, FIGS. 4A, 4B and 4C) is generally cylindrical in shape and has a substantially central cylindrical cavity 66. The carrier anterior section cavity 64 and the carrier medial section cavity 66 are preferably in communication with one another. In one preferred embodiment of the present invention, a healing screw 20 (see FIG. 3) resides in the cavities 64 and 66, and a layer of adhesive paper 22 (see FIGS. 2 and 3) or the like is removably attached to the top of the anterior section 26. The paper layer 22 prevents the healing screw 20 from falling out of the carrier 12. Optionally, the paper layer 22 may include a tab 24 to facilitate its removal from the carrier 12.

Referring to FIGS. 4B and 4C, the internal wall 72 of the cavity 66 of the carrier medial section 28 is, preferably, disposed with a plurality of fingers, such as the fingers 80a, 80b and 80c. Preferably, the fingers 80a, 80b and 80c are flexible, and hence resiliently displaceable relative to the internal wall 72 of the carrier medial section 28. In one preferred embodiment, the carrier 12 includes the three fingers 80a, 80b and 80c, but as will be readily apparent to those of ordinary skill in the art, more or fewer fingers may be utilized with efficacy, as needed or desired. Preferably, the fingers 80a, 80b, 80c are arranged in a substantially symmetrical fashion and substantially equidistantly spaced from their respective neighboring fingers. Preferably, and as shown in FIGS. 4B and 4C, the fingers 80a, 80b, 80c extend in a direction away from the carrier anterior section 26.

Alternatively, the fingers may be configured to extend in the direction towards the carrier anterior section 26.

Referring in particular to FIGS. 4B and 4C, preferably, each one of the fingers 80a, 80b, 80c has a respective top end 82a, 82b, 82c, respective body portion 84a, 84b, 84c, and respective bottom end 86a, 86b, 86c. Each of the finger top ends 82a, 82b, 82c is attached to the carrier internal wall 72, and is preferably curved to generally follow the curvature of the internal wall 72. In one preferred embodiment of the present invention, the fingers 80a, 80b, 80c are molded into the carrier 12. Functionally, the finger top ends 82a, 82b, 82c serve the purpose of attaching the respective fingers 80a, 80b, 80c to the carrier internal wall 72 and of spacing the respective displaceable body portions 84a, 84b, 84c and bottom ends 86a, 86b, 86c of the respective fingers 80a, 80b, 80c from the carrier internal wall 72.

Preferably, the body portions 84a, 84b, 84c of the respective fingers 80a, 80b, 80c extend in a direction away from the respective top ends 82a, 82b, 82c (FIGS. 4B, 4C). The finger body portions 84a, 84b, 84c are preferably spaced from the carrier internal wall 72 to create clearance space for the resilient displacement of the fingers 80a, 80b, 80c. Preferably, the finger body portions 84a, 84b, 84c are curved to generally follow the curvature of the carrier internal wall 72.

Referring in particular to FIGS. 4B and 4C, preferably, the bottom ends 86a, 86b, 86c of the respective fingers 80a, 80b, 80c bulge or project generally radially inwards into the cavity 66 of the carrier medial section 28, and are generally thicker than the respective finger body portions 84a, 84b, 84c. The finger bottom ends 86a, 86b, 86c are preferably spaced from the carrier internal wall 72 to create clearance space for the resilient displacement of the fingers 80a, 80b, 80c. Preferably, the fingers 80a, 80b, 80c, including the finger bottom ends 86a, 86b, 86c are curved to generally follow the curvature of the carrier internal wall 72 to form a detent mechanism for relative engagement. As will be discussed in more detail later herein, the bulging or projecting of the finger bottom ends 86a, 86b, 86c cooperates with an annular or circumferential groove 42 formed on the insertion tool screw 14 (FIG. 3) to lock the screw 14 into the carrier 12.

Preferably, and referring to FIGS. 4A, 4B and 4C, the posterior section 30 of the carrier 12 includes an exterior lip 76, an upper substantially cylindrical cavity 70, and an internal substantially hexed central cavity 68. The outer part of the posterior section 30 below the lip 76 is generally cylindrical in shape, and preferably has a slight taper extending in the direction away from the lip 76 below the cavity 70. The lip 76 serves as a seat for an insert (not shown) which circumscribes the carrier medial section 28 and permits the dental implant kit 10 (see FIG. 2) to be packaged in a vial (not shown). Preferably, the carrier posterior section hexed cavity 68 and the carrier posterior section cylindrical cavity 70 are in communication and their junction defines a step 34. The carrier posterior section cavity 70 is in communication with the carrier medial section cavity 66. The hexed cavity 68 permits the carrier 12 to substantially irrotationally mate with the insertion tool (see FIGS. 2 and 3), as will be discussed later herein, though those skilled in the art will readily comprehend that the cavity 68 may be alternately shaped, as required or desired.

Figure 5:
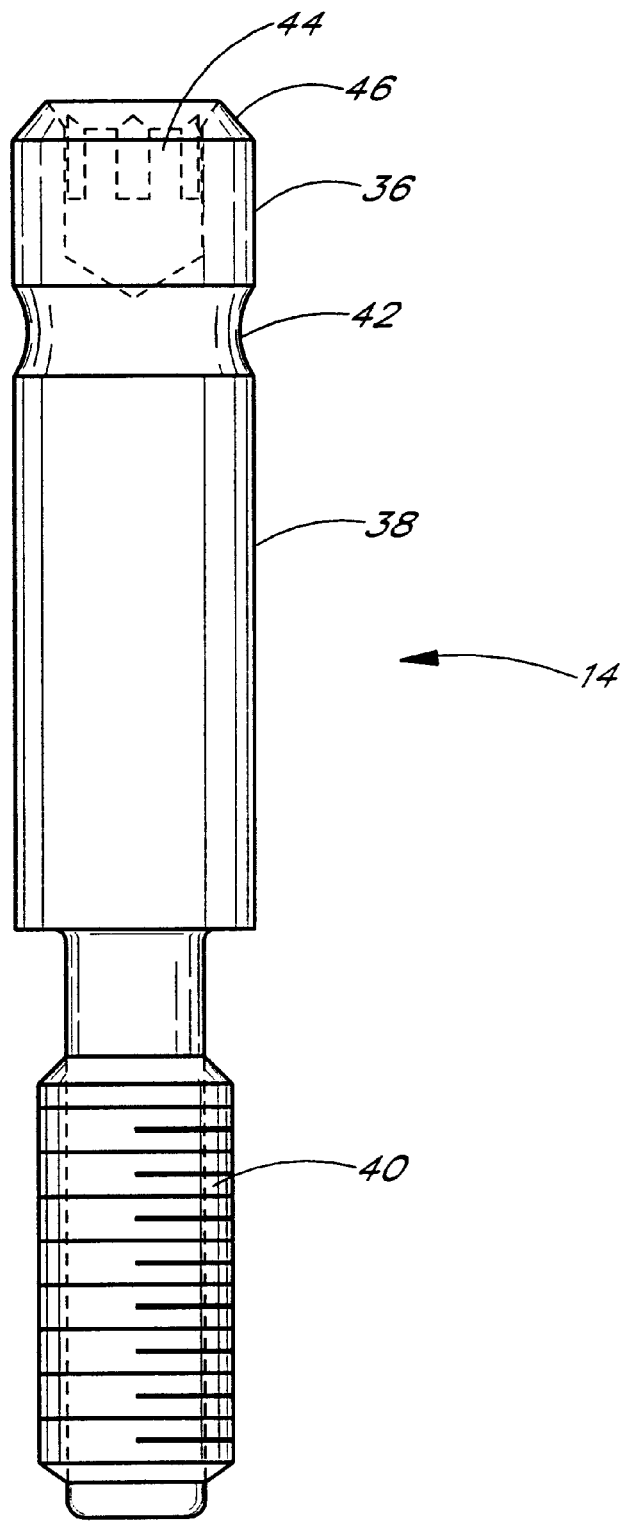
FIG. 5 is a side elevation view of the screw of FIG. 3.
Figure 6:
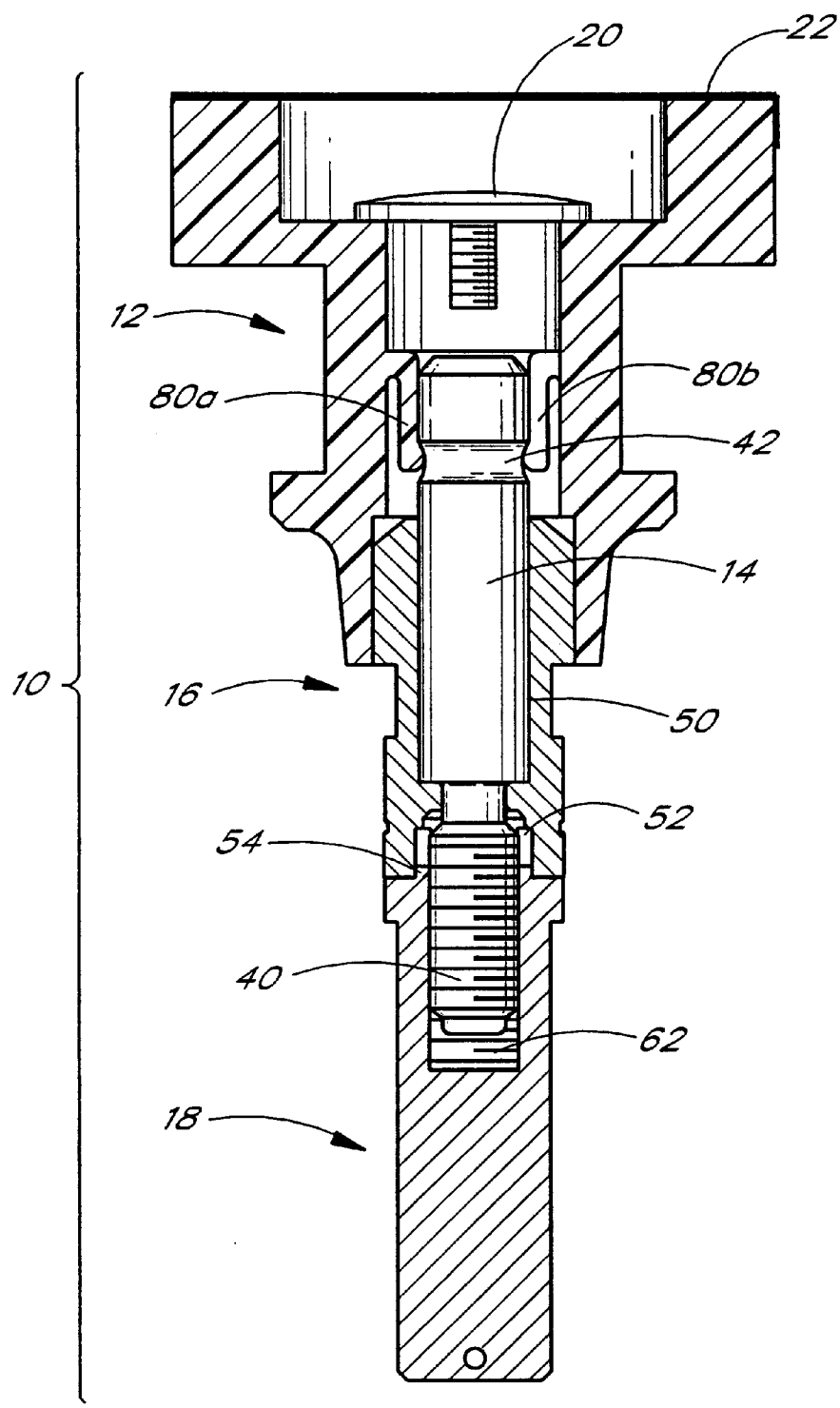
FIG. 6 is a partially sectional view illustrating the engagement of the carrier and screw of FIG. 3.

The insertion tool screw 14, shown, for example, in FIGS. 3 and 5, preferably, includes a head 36 with a substantially hexed socket 44, a groove 42, a body portion 38, and a lower threaded portion 40. Preferably, the top of the screw head 36 has a taper 46, in the direction moving away from the screw body portion 38, which assists in inserting the screw head 36 within the carrier fingers 80a, 80b, 80c (shown, for example, in FIGS. 4B and 4C). Preferably, the groove 42 is positioned below and proximate to the screw head 36. The groove 42 of the screw 14 is preferably substantially circumferential and engages the bulging or projecting finger bottom ends 86a, 86b, 86c (shown, for example, in FIGS. 4B and 4C) when the dental implant kit 10 is in an assembled state, as illustrated in FIG. 6. The threaded portion 40 of the screw 14 threadably connects the screw 14 to the implant 18, as illustrated in FIG. 6.

Those skilled in the art will readily recognize that though the drawings illustrate the bulging finger bottom ends 86a, 86b, 86c to be generally bulbous and the screw groove 42 to be generally circumferential or annular, alternate configurations may be employed giving due consideration to the goals of providing a reliable and releasable mechanical lock for holding the implant 18. Of course, the groove 42 may also be placed on any one of the components forming an implant assembly. For example, the groove 42 may be placed on the insertion tool 16. The implant assembly, as illustrated in the drawings includes the insertion tool screw 14, the insertion tool 16, and the implant 18, though it can include fewer or more components. Also, one or more components may be combined, as desired, to form an integral assembly.

Preferably, and referring particularly to FIGS. 2, 3 and 6, the insertion tool 16 has a substantially hexagonal upper portion 48 which is dimensioned to form a substantially irrotational close tolerance fit in the substantially hexed cavity 68 of the carrier posterior section 30. The insertion tool 16 also includes a substantially central cavity 50 (see FIG. 6) which permits the insertion tool screw 14 to traverse through the insertion tool and threadably mate with implant 18. The insertion tool cavity 50 includes at its lower end a substantially hexagonal socket 52 which allows substantially irrotational mating between the insertion tool 16 and the implant 18.

Preferably, and referring particularly to FIGS. 2, 3 and 6, the implant includes a substantially hexagonal post 54, a substantially central threaded cavity 62 and a threaded portion 56. The implant hexagonal post 54 is located at the upper end of the implant 18 and mates with the hexagonal socket 52 of the insertion tool to provide a substantially irrotational engagement The implant threaded cavity 62 threadably engages the threaded portion 40 of the insertion tool screw 14. The implant threaded portion 56 permits the implant to be threadably inserted into an osteotomy in the jaw bone of a patient. The implant 18 may further include a pair of cutting edges 58 having recesses 59 (only one of each is visible in FIGS. 2 and 3) with a through hole 60, which are configured in a manner that is well known in the art.

The implant carrier 12, shown, for example, in FIGS. 4A, 4B and 4C, is preferably fabricated from a thermoplastic, though other suitable plastics, metals, alloys and ceramics may be utilized with efficacy, giving due consideration to the goals of providing flexible fingers and durability. In one preferred form of the invention, the implant carrier 12 is fabricated from a nylon such as ultramid B3WG5 nylon 6. Alternatively, the fingers 80a, 80b, 80c of the carrier 12 may be fabricated from a material different than the rest of the carrier 12, as needed or desired. Preferably, and referring, for example, to FIG. 3, the insertion tool screw 14, the insertion tool 16 and the implant 18 are fabricated from pure titanium or titanium alloys, such as Ti-6Al-4V, which are compatible with bone, fixtures, tools, and the ultimate prosthesis, as well as being innocuous in use over time. Of course, the insertion tool screw 14, the insertion tool 16 and the implant 18 may be fabricated from other suitable metals, alloys and ceramics, as required or desired, giving due consideration to the goals of providing compatibility, inertness, corrosion-resistance and durability.

Referring in particular to FIGS. 3, 4A, 4B and 4C, preferably, the implant carrier 12 has an overall length of about 13.0 mm (0.510 inches) and a maximum diameter of about 12.7 mm (0.500 inches). Preferably, the carrier anterior section 26 has a maximum outer diameter of about 12.7 mm (0.500 inches) and a length of about 3.86 mm (0.152 inches), and the carrier anterior section cavity 64 has a maximum diameter of about 8.89 mm (0.35 inches) and is about 2.79 mm (0.110 inches) deep. Preferably, the carrier medial section 28 has an outer diameter of about 6.60 mm (0.26 inches) and a length of about 4.83 mm (0.190 inches), and the carrier medial section cavity 66 has a diameter of about 3.68 mm (0.145 inches) and is about 4.83 mm (0.190 inches) deep. Preferably, the carrier posterior section 30 has a maximum outer diameter of about 8.89 mm (0.350 inches) and a minimum outer diameter of about 5.59 mm (0.220 inches), due to the taper of about 5° below the lip 76, and an overall length of about 4.27 mm (0.168 inches). The lip 76 of the carrier posterior section 30 is, preferably, about 1.27 mm (0.050 inches) long and has a maximum outer diameter of about 8.89 mm (0.350 inches). Preferably, the carrier posterior section cylindrical cavity 70 has a diameter of about 3.68 mm (0.145 inches) and is about 1.27 mm (0.050 inches) deep. Preferably, the carrier posterior section hexed cavity 68 is about 3.00 mm (0.118 inches) deep with each wall that creates the hexagonal shape being approximately 2.29 mm (0.09 inches) wide.

Referring to FIGS. 4A, 4B and 4C, preferably, the fingers 80a, 80b, 80c are located about 3.00 mm (0.118 inches) deep in the carrier medial section cavity 66, and have a length of about 2.87 mm (0.113 inches). The finger top ends 82a, 82b, 82c are, preferably, about 0.889 mm (0.035 inches) long and have a maximum thickness of about 0.584 mm (0.023 inches). The finger body portions 84a, 84b, 84c are, preferably, about 1.25 mm (0.049 inches) long and have a maximum thickness of about 0.330 mm (0.013 inches). The finger bottom ends 86a, 86b, 86c are, preferably, about 0.737 mm (0.029 inches) long and have a maximum thickness of about 0.559 mm (0.022 inches). The finger body portions 84a, 84b, 84c and finger bottom ends 86a, 86b, 86c are spaced from the carrier medial section wall 72 by a distance of about 0.533 mm (0.021 inches). In the unflexed state, the finger top ends 82a, 82b, 82c and finger body portions 84a, 84b, 84c generally envelop a generally cylindrical region with a diameter of about 2.49 mm (0.098 inches). In the unflexed state, the finger bottom ends 86a, 86b, 86c generally envelop a generally cylindrical region with a diameter of about 2.03 mm (0.080 inches), and extend about 0.229 mm (0.009 inches) further into the medial section cavity 68 relative to the finger body portions 84a, 84b, 84c. Preferably, when the fingers 80a, 80b, 80c are flexed, during engagement and disengagement with the insertion tool screw 14, they can provide an interference slip of up to about 15%.

Referring in particular to FIGS. 3, 5 and 6, preferably, the insertion tool screw 14 is about 15.2 mm (0.600 inches) long. Preferably, the screw head 36 has a maximum diameter of about 2.44 mm (0.096 inches), thereby permitting it to be captured in a substantially close tolerance fit between the generally cylindrical region of about 2.49 mm (0.098 inches) diameter formed between finger top ends 82a, 82b, 82c and finger body portions 84a, 84b, 84c, as can best be seen in FIG. 6. Preferably, the groove 42 of the screw 14 is recessed inwards by a maximum of 0.178 mm (0.007 inches), thereby having a maximum diameter of about 2.44 mm (0.096 inches) and a minimum diameter of about 2.08 mm (0.082 inches). Thus, when the bulging finger bottom ends 86a, 86b, 86c, which form a generally cylindrical region of about 2.03 mm (0.080 inches) diameter, engage the groove 42 in the assembled dental implant kit 10 (see FIG. 2), the fingers 80a, 80b, 80c will be slightly flexed outwards by a distance of about 0.051 mm (0.002 inches). The threaded portion 40 of the screw 14 has a diameter of about 1.88 mm (0.074 inches) and a length of about 4.57 mm (0.180 inches). The insertion tool 16 and the implant 18 (see, for example FIGS. 3 and 6) are accordingly dimensioned so as to accommodate the carrier 12 and screw 14, in the manner best illustrated by FIG. 6.

Figure 1A:
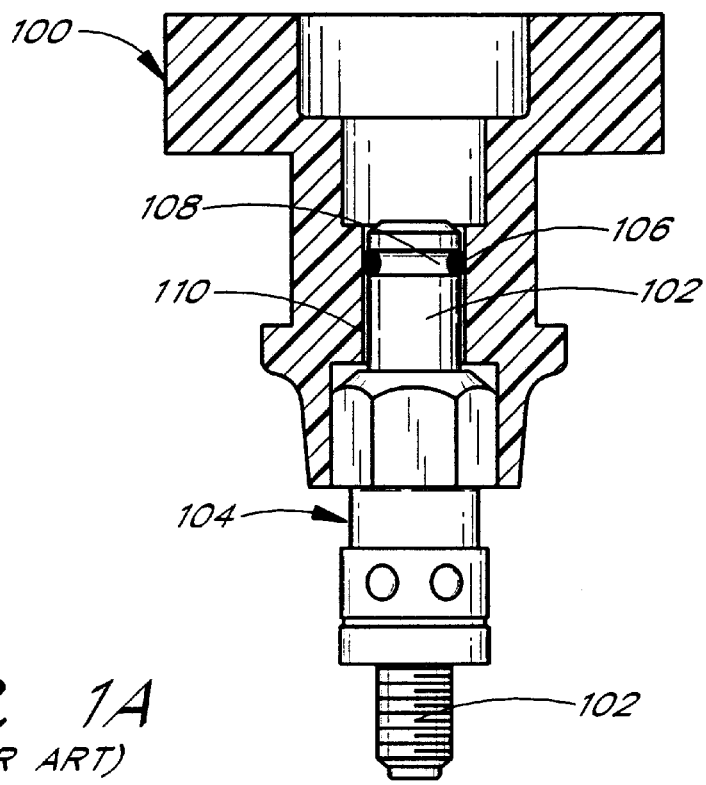
FIG. 1A is a partially sectional side view illustrating the engagement of a dental implant carrier with an insertion tool screw, as known in the prior art.
Figure 1B:
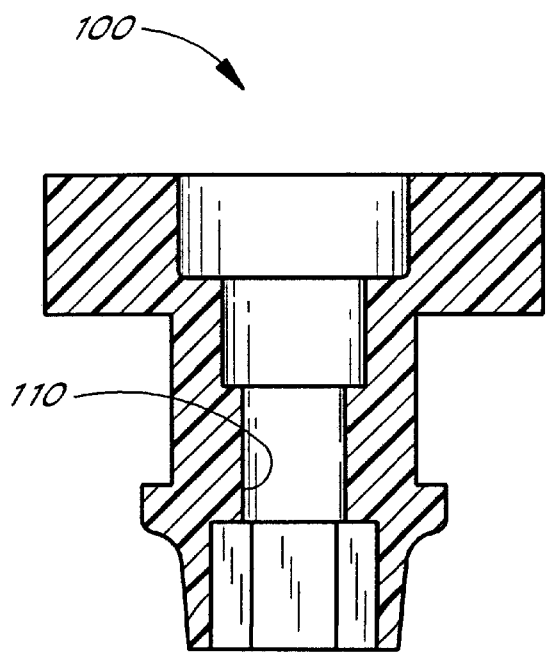
FIG. 1B is a sectional view illustrating the carrier of FIG. 1A.

Referring to the drawings, and particularly to FIGS. 2, 3 and 6, the carrier 12 of the dental implant kit 10 provides several benefits and advantages over the prior art implant carrier (shown in FIGS. 1A and 1B). Advantageously, the carrier fingers 80a, 80b, 80c engage the insertion tool screw 14 by a redundant latching mechanism which is a combination of providing a mechanical lock and applying a compressive generally radial force. The mechanical lock is provided by the engagement of the bulging or projecting bottom ends 86a, 86b, 86c of the respective fingers 80a, 80b, 80c with the groove 14 of the insertion tool screw 14. The radial compressive force is provided due to the outward flexing of the resilient fingers 80a, 80b, 80c when the screw 14 is captured in the carrier 12. Advantageously, the fingers 80a, 80b, 80c are only slightly flexed in the assembled state of the dental implant kit 10 since the resilient displacement of the fingers 80a, 80b, 80c is preferably only about 0.051 mm (0.002 inches) when the screw 14 is gripped in the carrier 12. Desirably, this minimizes the "deformation" or "pre-stressing" of the fingers 80a, 80b, 80c in the assembled state and permits a substantially long on-the-shelf and storage life for the dental implant kit 10. It will be apparent to those skilled in the art that the present invention may be practiced with the carrier fingers 80a, 80b, 80c configured to apply less, more or no radial compressive force on the screw 14, as required or desired. Of course, in the latter case of no radial compressive force, the fingers 80a, 80b, 80c will be substantially unflexed in the assembled state of the dental implant kit 10. The resiliency of the fingers 80a, 80b, 80c permits insertion and removal of the screw 14 from the carrier 12. During the insertion of the screw 14 in the carrier 12, preferably via the carrier posterior section 30, the fingers 80a, 80b, 80c initially flex generally radially outwards and receive the screw head 36 until the bulging finger bottom ends 86a, 86b, 86c lock into the screw groove 42 as the fingers 80a, 80b, 80c are resiliently displaced inwards. During the removal of the screw 14 from the carrier 12, preferably via the carrier posterior section 30, again the fingers 80a, 80b, 80c flex generally radially outwards with the bulging or projecting finger bottom ends 86a, 86b, 86c slipping out of the screw groove 42 as the fingers 80a, 80b, 80c are resiliently displaced inwards, hence releasing the screw head 36, and allowing detachment of the screw 14 from the carrier 12. Advantageously, the preferred generally bulbous shape of the finger bottom ends 86a, 86b, 86c, provides a camming action, during removal (and insertion) of the screw 14 from the carrier 12, that facilitates this same removal (and insertion).

In use, and referring to FIGS. 2, 3 and 6 in particular, after the dental implant kit is typically removed from a sterile vial or packing (not shown) it is manually held via the carrier anterior section 26 while the adhesive paper layer 22 is peeled off the carrier 12 and the healing screw 20 is removed from the carrier 12. At this stage, the carrier 12 is reliably and releasably holding the implant assembly, preferably, comprising the insertion tool screw 14, the insertion tool 16, and the implant 18. The dental implant kit 10 is transported to the surgical site with the carrier anterior section 26 being manually held. Since the fingers 80a, 80b, 80c reliably grip the screw 14, the implant 18 is prevented from coming loose from the dental implant kit 10. While still manually holding the carrier anterior section 26, the implant 18 is inserted into the osteotomy in the patient's jaw bone and by rotating the carrier anterior section 26 the implant is threaded into the osteotomy. The carrier 12 may be used to drive the implant 18 fully in the osteotomy, after which it is detached from the screw 14 by pulling and/or shaking it off the screw 14. During removal of the carrier 12 from the screw 14 the carrier fingers 80a, 80b, 80c flex in the manner that has been described herein above and permit the release of the screw 14 from the carrier 12. The driving force for implant insertion is transferred from the carrier 12 to the implant 18 via the insertion tool 16 which is at its hexagonal upper portion 48 locked in the carrier hexed cavity 68 and at its lower end substantially irrotationally mated with the implant 18 by means of the insertion tool hexagonal socket 52 and the implant hexagonal post 54. In some cases, after the implant 18 has been partially threaded into the osteotomy by the carrier, additional torque not conveniently implemented by the carrier 12 may be required. In this situation, the carrier 12 may be detached from the screw 14 and a wrench (not shown), which engages the hex socket 44 of the screw 14, may be used to thread the implant 18 further in the osteotomy until the implant 18 is properly seated in the required position. Once the implant 18 has been positioned in the osteotomy and the carrier 12 removed from the screw 14, the screw 14 and the insertion tool 16 are detached from the implant 18 and replaced by the healing screw 20. The carrier 12, insertion tool screw 14 and the insertion tool 16 are typically discarded at this stage.

The utility of the present invention will be readily apparent to those skilled in the art. The dental implant carrier of this invention reliably permits a dental implant to be transported to an osteotomy by providing flexible locking and gripping fingers which maintain their resilience over substantial periods of on-the-shelf and storage time, thereby substantially enhancingly shielding the patient from the potential hazards discussed herein before.

While the present invention has been described with a certain degree of particularity, it is manifest that many changes may be made in the specific designs, constructions and methodology hereinabove described without departing from the spirit and scope of this disclosure. It is understood that the invention is not limited to the embodiments set forth herein for purposes of exemplification, but is to be defined only by a fair reading of the appended claims, including the full range of equivalency to which each element thereof is entitled.

What is claimed is:

1. A dental implant assembly, comprising:
    a dental implant comprising a threaded portion adapted to be received in an osteotomy and a threaded cavity;
    a screw comprising a head, a groove and a threaded portion threadably engaged with said threaded cavity of said dental implant; and
    a carrier comprising a plurality of flexible fingers having projecting portions engaged with said groove of said screw to reliably and releasably hold said dental implant.

2. The dental implant assembly of claim 1, further comprising an insertion tool substantially irrotationally engaged with said carrier and said dental implant.

3. The dental implant assembly of claim 1, wherein said fingers are attached to an internal wall of said carrier.

4. The dental implant assembly of claim 3, wherein said fingers are spaced from said internal wall of said carrier.

5. The dental implant assembly of claim 1, wherein said projecting portions of said fingers mechanically lock into said screw.

6. The dental implant assembly of claim 1, wherein said fingers grip said screw by applying a substantially radial compressive force.

7. The dental implant assembly of claim 1, wherein said fingers are fabricated from a thermoforming plastic.

8. The dental implant assembly of claim 1, wherein said fingers are molded into said carrier.

9. The dental implant assembly of claim 1, wherein said fingers are substantially equidistantly and symmetrically spaced.

10. The dental implant assembly of claim 1, wherein said plurality of fingers comprises three fingers.

11. The dental implant assembly of claim 1, wherein said groove of said screw is substantially circumferential.

12. A dental implant kit, comprising:
    a carrier comprising a plurality of internal resilient fingers having projecting portions;
    an insertion tool adapted to substantially irrotationally engage said carrier and comprising a substantially central cavity;
    a screw sized and configured to at least partially reside in said cavity of said insertion tool and comprising a groove adapted to engage said projecting portions of said fingers of said carrier;
    an implant adapted to substantially irrotationally couple with said insertion tool and comprising a threaded socket sized and configured to threadably engage said screw;
    whereby, said carrier can reliably and releasably hold said implant.

13. The dental implant kit of claim 12, wherein said fingers are attached to and spaced from an internal wall of said carrier.

14. The dental implant kit of claim 12, wherein said fingers are adapted to mechanically lock into said screw.

15. The dental implant kit of claim 12, wherein said fingers are adapted to grip said screw by applying a substantially radial compressive force.

16. The dental implant kit of claim 12, wherein said fingers are fabricated from a thermoplastic.

17. The dental implant kit of claim 12, wherein said fingers are molded into said carrier.

18. The dental implant kit of claim 12, wherein said fingers are substantially equidistantly and symmetrically spaced.

19. The dental implant kit of claim 12, wherein said plurality of fingers comprises three fingers.

20. The dental implant kit of claim 12, wherein said groove of said screw is substantially circumferential.

21. A carrier for reliably and releasably holding a dental implant, comprising:
    a substantially central cavity having an internal wall; and
    a plurality of flexible fingers disposed within said cavity, said fingers having top ends attached to said wall so that said fingers are slightly spaced from said wall, said fingers having body portions which are generally curved and extend downwards, said fingers having bottom ends which bulge generally radially into said cavity.

22. The carrier of claim 21, wherein said fingers are adapted to mechanically lock into an insertion tool screw threadably engaged with said dental implant.

23. The carrier of claim 22, wherein said insertion tool screw comprises a groove for engaging said fingers.

24. The carrier of claim 23, wherein said groove is substantially circumferential.

25. The carrier of claim 21, wherein said fingers are adapted to grip an insertion tool screw threadably engaged with said dental implant by applying a substantially radial compressive force.

26. The carrier of claim 25, wherein said insertion tool screw comprises a groove for engaging said fingers.

27. The carrier of claim 26, wherein said groove is substantially circumferential.

28. The carrier of claim 21, wherein said fingers are fabricated from a thermoforming plastic.

29. The carrier of claim 21, wherein said fingers are molded into said carrier.

30. The carrier of claim 21, wherein said fingers are substantially equidistantly and symmetrically spaced.

31. The carrier of claim 21, wherein said plurality of fingers comprises three fingers.

32. A dental implant assembly, comprising the carrier of claim 21, an insertion tool, an insertion tool screw and an implant.

33. A dental implant kit, comprising the carrier of claim 21, an insertion tool, an insertion tool screw and an implant.

34. A combination of a carrier and a dental implant, said carrier comprising a plurality of internal flexible fingers for releasably capturing said dental implant, and said dental implant being releasably connected thereto.

35. The combination of claim 34, wherein said fingers are adapted to mechanically lock into an insertion tool screw threadably engaged with said dental implant.

36. The combination of claim 35, wherein said insertion tool screw comprises a groove for engaging said fingers.

37. The combination of claim 36, wherein said groove is substantially circumferential.

38. The combination of claim 34, wherein said fingers are adapted to grip an insertion tool screw threadably engaged with said dental implant by applying a substantially radial compressive force.

39. The combination of claim 38, wherein said insertion tool screw comprises a groove for engaging said fingers.

40. The combination of claim 39, wherein said groove is substantially circumferential.

41. The combination of claim 34, wherein said fingers are fabricated from a thermoplastic.

42. The combination of claim 34, wherein said fingers are molded into said carrier.

43. The combination of claim 34, wherein said fingers are substantially equidistantly and symmetrically spaced.

44. The combination of claim 34, wherein said plurality of fingers comprises three fingers.

45. A dental implant assembly, comprising the combination of claim 34, an insertion tool and an insertion tool screw.

46. The combination of claim 34, further comprising an insertion tool and an insertion tool screw.

47. A carrier for a dental implant kit assembly, comprising:

an anterior section being generally cylindrical in shape and having a substantially central cylindrical cavity, at least part of the outer surface of said carrier anterior section being either ridged, grooved or knurled to facilitate manual manipulation by providing a gripping surface;

a medial section being generally cylindrical in shape and having a substantially central cylindrical cavity, said anterior section cavity and said medial section cavity being in communication, a wall of said medial section cavity being disposed with a plurality of flexible fingers, said fingers being generally equidistantly and symmetrically spaced relative to one another, top ends of said respective fingers being attached to said wall of said medial section cavity so that said respective fingers are slightly spaced from said medial section cavity wall, body portions of said respective fingers extending in a direction away from said anterior section, said body portions of said respective fingers being generally curved substantially parallely to said wall of said medial section cavity, bottom ends of said fingers being generally thicker than said body portions of said respective fingers and bulging generally radially inwardly into said medial section cavity, said bottom ends of said respective fingers being sized and shaped to engage a substantially circumferential groove formed on at least one portion of said dental implant kit/assembly, said fingers mechanically locking into said groove;

a posterior section having a lip adjacent to said carrier medial section and being generally taperingly cylindrical in shape, said posterior section having an upper substantially central cylindrical cavity and a lower substantially central hexagonal cavity, said posterior section upper cavity being in communication with said medial section cavity, said posterior section lower hexagonal cavity being sized and shaped to substantially irrotationally engage an insertion tool of said dental implant kit/assembly;

whereby, said carrier reliably and releasably facilitates transfer of said dental implant to a surgical site, and insertion of said dental implant into an osteotomy in a jaw bone.

48. The carrier of claim 47, wherein said fingers are fabricated from nylon.

49. The carrier of claim 47, wherein said fingers are fabricated from a thermoplastic.

50. The carrier of claim 47, wherein said fingers are molded into said carrier.

51. The carrier of claim 47, wherein said plurality of fingers comprises three fingers.

52. The carrier of claim 47, wherein said groove is formed on an insertion tool screw of said dental implant kit/assembly.

53. A method of using a carrier for a dental implant, comprising the steps of:

holding said dental implant by manually gripping an anterior section of said carrier;

transporting said dental implant to an osteotomy, said carrier having a plurality of internal flexible fingers to reliably and releasably engage a groove of a screw threadably engaged with said dental implant;

inserting said dental implant in the osteotomy;

rotating said carrier anterior section to thread said dental implant in the osteotomy until said dental implant is seated in the osteotomy; and removing said carrier from said screw, said fingers being flexed outwards during said step of removing.

54. A method of delivering a dental implant to an osteotomy at a surgical site, comprising the steps of:

holding said dental implant by gripping a carrier having a plurality of flexible fingers releasably engaged with a screw threadably engaged with said dental implant;

transporting said dental implant to said osteotomy;

inserting said dental implant in said osteotomy;

rotating said carrier to thread said dental implant in said osteotomy until said dental implant is at least partially seated in said osteotomy; and detaching said carrier from said dental implant by manipulating said carrier to disengage said fingers from said screw.

* * * * *